US006440938B1

(12) United States Patent
Garrod et al.

(10) Patent No.: US 6,440,938 B1
(45) Date of Patent: Aug. 27, 2002

(54) PREVENTION AND/OR TREATMENT OF ALLERGIC CONDITIONS

(75) Inventors: David R. Garrod, Cheshire; Clive Robinson, London, both of (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/581,075

(22) PCT Filed: Dec. 11, 1998

(86) PCT No.: PCT/GB98/03721

§ 371 (c)(1),
(2), (4) Date: Aug. 10, 2000

(87) PCT Pub. No.: WO99/29339

PCT Pub. Date: Jun. 17, 1999

(30) Foreign Application Priority Data

Dec. 11, 1997 (GB) .............................................. 9726114

(51) Int. Cl.[7] ........................ A61K 38/00; A61K 31/255

(52) U.S. Cl. .......................... 514/19; 514/18; 514/517; 514/518

(58) Field of Search ............................... 514/18, 19, 2, 514/8, 12, 21, 330, 534, 530, 327, 336–331, 328–329; 530/331; 206/828

(56) References Cited

U.S. PATENT DOCUMENTS 5,166,134 A * 11/1992 Lezdey et al. .................. 514/8
6,034,066 A * 3/2000 Johnson et al. ................ 514/18

OTHER PUBLICATIONS

"Allergens of the house–dust mite", Khgatian et al., 1995, Academy Medical Sciences: Abstract.*
Komiyama et al, "Inhibition of Cysteine and Serine Proteinase by the Cowpox Virus Serpin CRMA", Intracellular Protein Catabolism 21:173–176 (1996).
Oppert et al, "Dietary Mixtures of Cysteine and Serine Proteinase Inhibitors Exhibit Synergistic Toxicity Toward the Red Four Beetle, *Tribolium Castaneum*", Comp. Biochem. Physiol. 105C(3):379–385 (1993).
Kalsheker et al, "The House Dust Mite Allergen Der p1 Catalytically Inactivates α1–Antitrypsin by Specific Reactive Centre Loop Cleavage: A Mechanism That Promotes Airway Inflammation and Asthma", Biochemical and Biophysical Research Communications 221:59–61 (1996).
Stewart et al, "Faecally Derived Hydrolytic Enzymes from *Dermatophagoides pteronyssinus*: Physicochemical Characterisation of Potential Allergens", Int. Arch. Allergy Appl. Immunol. 95:248–256 (1991).
Hewitt et al, "Heterogeneous proteolytic specificity and activity of the house dust mite proteinase allergen Derp1", Clinical and Experimental Allergy 27:201–207 (1997).

Proteolytic Enzymes A Practical Approach, The Practical Aproach Series, Rickwood and Hames, eds, Appendix III, p. 245.
Gebhard et al, "Biochemistry of aprotinin and aprotinin–like inhibitors", Proteinase Inhibitors, Chapter 10, pp. 375–388 (1986).
Barrett et al, "L–trans–Epoxysuccinyl–leucylamido(4–guanidino)butane (E–64) and its analogues as inhibitors of cysteine proteinases including cathepsins B, H and L", Biochem J. 201:189–198 (1982).
Shaw and Green, "Inactivation of Thiol Proteases with Peptidyl Diazomethyl Ketones", Methods in Enzymology 80:820–826 (1981).
Anastasi et al, "Cystatin, a protein inhibitor of cysteine proteinases", Biochem J. 211:129–138 (1983).
Schoellmann and Shaw, "Direct Evidence for the Presence of Histidine in the Active Center of Chymotrypsin", Biochemistry 2(2):252–255 (1963).
Shaw et al, "Evidence for an Active–Center Histidine in Trypsin through Use of a Specific Reagent, 1–Chloro–3–tosylamido–7–amino–2–heptanone, the Chloromethyl Ketone Derived from $N^\alpha$–Tosyl–L–lysine", Biochemistry 4(10):2219–2224 (1965).
James, "Inactivation of the Protease Inhibitor Phenylmethylsulfonyl Fluoride in Buffers", Analytical Biochemistry 86:574–579 (1978).
Fahrney and Gold, "Sulfony Fluorides as Inhibitors of Esterases. I. Rates of Reaction with Acetylcholinesterase, α–Chymotrypsin, and Trypsin", J. Am. Chem. Soc. 85:997–1000 (1963).
Umezawa, "Structures and Activities of Protease Inhibitors of Microbial Origin", Naturally Ocurring Protease Inhibitors, Methods in Enzymol. Chapter 55:678–695 (1972).
Laura et al, "(p–Amidinophenyl)methanesulfonyl Fluoride, an Irreversible Inhibitor of Serine Proteases", Biochemistry 19:4859–4864 (1980).
Harper et al, "Reactionof Serine Protease with Substituted Isocnoumarins: Discovery of 3,4–Dichloroisocoumarin, a New General Mechanism Based Serine Protease Inhibitor", Biochemistry 4:1831–1841 (1985).
Barrett, "The cystatins: A diverse superfamily of cysteine peptidase inhibitors", Biomed. Biochim. Acta 45:11–12):1363–1374 (1986).

(List continued on next page.)

Primary Examiner—Zohreh Fay
Assistant Examiner—Brian-Yong Kwon
(74) Attorney, Agent, or Firm—Nixon & Vanderhye P.C.

(57) ABSTRACT

The present invention relates to the use of an inhibitor of cysteine proteinase activity in conjunction with an inhibitor of any serine proteinase activity other than trypsin for the manufacture of a medicament for the prevention or treatment of a condition in which an allergen traverses an epithelial barrier such as asthma. Also included in the invention are formulations and kits containing serine and cysteine proteinase inhibitors and their use in the prevention or treatment of conditions in which an allergen traverses an epithelial barrier.

7 Claims, 8 Drawing Sheets

OTHER PUBLICATIONS

Figure 1:
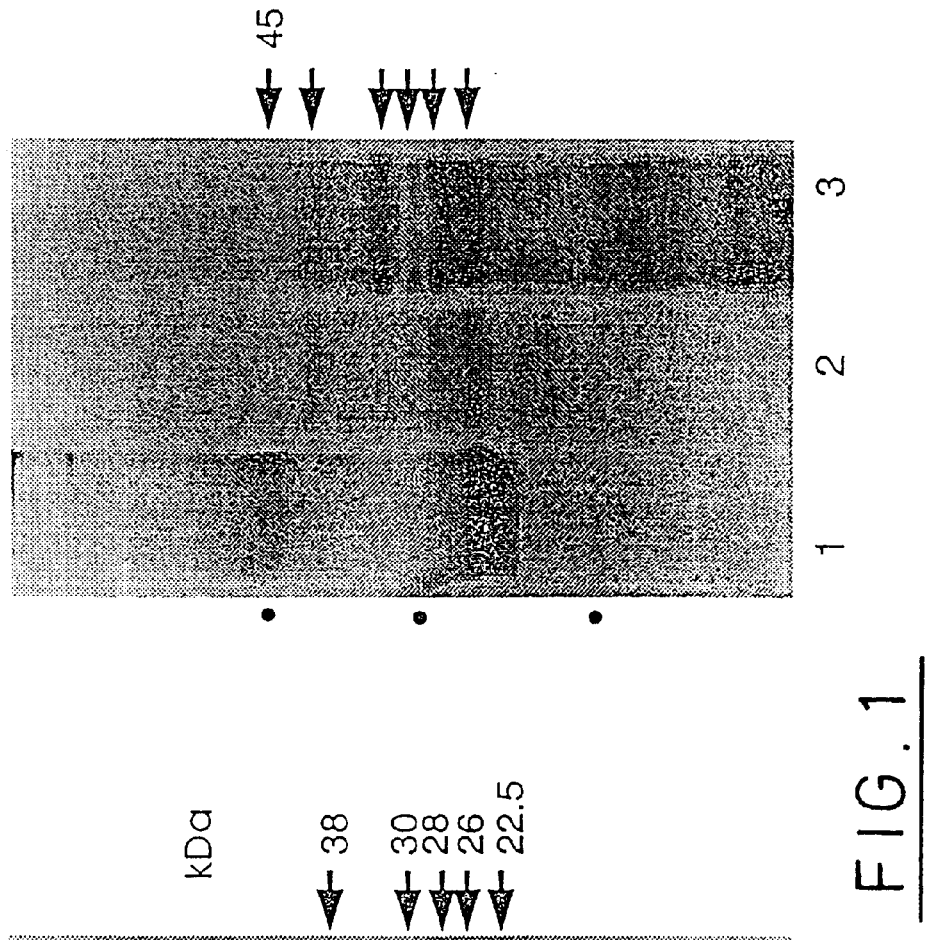
Figure 1:
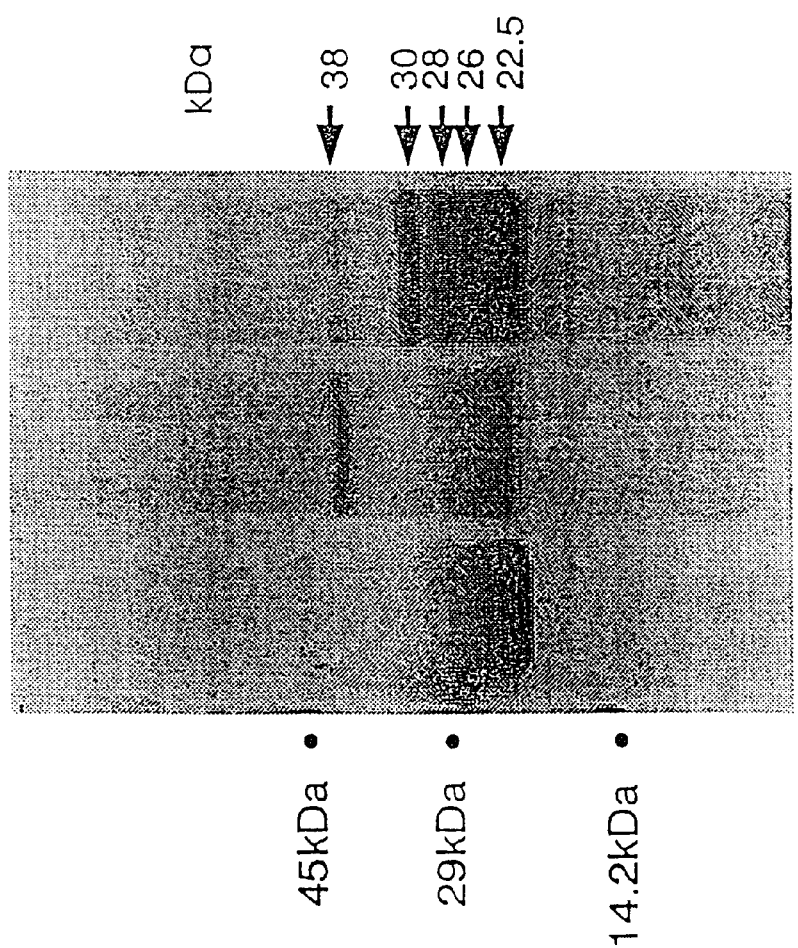

Birk, "Lima Bean Trypsin Inhibitors", Naturally Occurring Protease Inhibitors, Methods in Enzymol. Chapter 45:707–709 (1976).

Birk, "Trypsin and Chymotrypsin Inhibitors from Soybeans", Naturally Occurring Protease Inhibitors, Chapter 45:700–703 (1976).

Travis and Johnson, "Human $\alpha_1$–Proteinase Inhibitor", Methods in Enzymology 81:754–765 (1981).

Flippova et al, "L–Pyroglutamyl–L–phenylalanyl–L–leucine–p–nitroanilide–A Chromogenic Substrate for Thiol Proteinase Assay", Analytical Biochemistry 143:293–297 (1984).

Odake et al, "Human and Murine Cytotoxic T Lymphocyte Serine Proteases: Subsite Mapping with Peptide Thioester Substrates and Inhibition of Enzyme Activity and Cytolysis by Isocoumarins", Biochemistry 30(8):2217–2227 (1991).

Reers et al, "Synthesis and Characterisation of Novel Thrombin Inhibitors Based on 4–Amidinophenylalanine", J. Enzyme Inhibition 9:61–72 (1995).

Kettner and Shaw, "Inactivation of Trypsin–Like Enzymes with Peptides of Arginine Chloromethyl Ketone", Methods in Enzymology 80:826–842 (1981).

McConnell et al, "Inhibition Studies of Some Serine and Thiol Proteinases by New Leupeptin Analogues", J. Med. Chem. 36:1084–1089 (1993).

John et al, "Functional effects of the inhibition of the cysteine protease activity of the major house dust mite allergen Der p 1 by a novel peptide–based inhibitor", Clinical and Experimental Allergy 30:784–793 (2000).

* cited by examiner

PREVENTION AND/OR TREATMENT OF ALLERGIC CONDITIONS

This application is a 371 of PCT/GB98/03721, filed Dec. 11, 1998.

The present invention relates to the prevention and/or treatment of allergic conditions and more particularly to such conditions in which a potential allergen must traverse an epithelial barrier. The invention has particular, but not sole, application to the prevention and/or treatment of asthma.

Asthma is the most common chronic disease of childhood and a major debilitating and life threatening condition. It is characterised by acute hypersensitivity, chronic bronchial reactivity and damage and disruption to lung epithelium.

A primary risk factor for asthma is the sensitisation of the lung to airborne allergens such as proteins excreted in the faecal pellets of house dust mites (HDM) belonging to the genus Dermatophagoides (e.g. D pteronyssinus, D. Farinae). When inhaled, HDM faecal pellets impact upon the fluid-covered epithelial surface of large diameter airways. The resulting hydration of HDM faecal pellets will trigger a rapid and total discharge of the major allergenic proteins thus achieving a high local concentration of HDM proteins on the airway lining. Sensitisation involves allergen detection by antigen presenting cells which are normally protected from the environment by the lung epithelium. The mechanism by which the allergens are able to traverse the epithelial barrier is not fully understood.

There is now an increasing body of evidence that several major allergens from HDMs exhibit catalytic competence as enzymes and this has prompted suggestions that these enzymatic actions might be important in allergic sensitisation and to the perpetuation of established allergic inflammatory reactions.

Most data concerning proteinase activity in mite allergens currently relate to those of groups 1, 3, 6 and 9 from mites of the genus Dermatophagoides. The group 1 allergens are cysteine proteinases and have been the subject of greatest scrutiny whereas a lesser amount of information exists concerning the enzymatic effects of the group 3, group 6 and group 9 allergens which share sequence identity with archetypal serine proteinases and which are themselves catalytically competent.

It has been proposed that the cysteine proteinase activity is important in exacerbating the allergic response in asthma because it cleaves CD23, a low affinity IgE receptor, on the surface of antibody producing cells. Cleavage results in positive feedback that causes an increase in igE secretion, thus augmenting the allergic response. On this basis, WO-A-97/04004 (Peptide Therapeutics) proposes that inhibitors of cysteine proteinases may be used inter alia for asthma prophylaxis. However we do not believe that the mechanism proposed in WO-A-97/04004 is likely to operate in vivo. The reason for this is that all experiments on cleavage of CD23 have been carried out on cells in culture and the concentrations of Der p 1 required to produce cleavage were in our view unrealistically large. The cells concerned would, in vivo, be located in the tissues or the blood. It is, in our view, extremely unlikely that allergen concentrations would reach the levels required to produce CD23 cleavage on these locations. There is no evidence that they do, nor that CD23 cleavage takes place in vivo.

Kalsheker N. et al. (1996) Biochem. Biophys. Res. Comms. (USA) 221/1 pages 59-61 discloses that the serine proteinase $\alpha_1$-antitrypsin protects the lower respiratory tract from damage by proteinases released in the lung during inflammation. The cysteine proteinase Der p1 is shown to cleave the proposed reactive loop of the serine proteinase inhibitor $\alpha_1$-antitrypsin and this mechanism is proposed as being important in the pathogenesis of asthma. Also disclosed is that $\alpha_1$-antitrypsin deficiency is linked to the incidence of childhood asthma. However there is no disclosure of how allergic conditions (such as asthma) in which an allergen must traverse an epithelial barrier may be treated or prevented.

Stewart G. et al. (1991)Int. Arch. Allergy Appl. Immunol. 95/2-3 pages 248–256 discloses that dust mite faeces contains three serine proteinases and a cysteine proteinase along with various other enzymes. It also discloses that the cysteine proteinase and at least one of the serine proteinases are allergenic. However there is no disclosure of how allergic conditions such as asthma in which an allergen must traverse an epithelial barrier may be treated or prevented.

In spite of the considerable effort which has taken place in the field of asthma research, there remains a need for improved methods for the prevention and/or treatment of asthma (and other allergic conditions in which a potential allergen most traverse an epithelial barrier).

In its first, broadest aspect the invention provides for the prevention and/or treatment of allergic conditions (of the type in which a potential allergen must traverse an epithelial barrier) by the inhibition of cysteine proteinase activity and serine proteinase activity.

The invention is applicable particularly (but not exclusively) to the treatment of asthma for which the cysteine proteinase activity to be inhibited is preferably that of Der p 1 whereas the serine proteinase activity to be inhibited may be that of any serine proteinase other than trypsin, preferably an allergen serine proteinase and more preferably Der p 3, Der p 6 and/or Der p 9.

The invention has been based on our experimental studies (set out in more detail below) which have demonstrated that the key initial step in allergic sensitisation to house dust mite allergens is mediated by both cysteine and serine proteinase activity. We have found that this activity causes disruption of tight junctions between the cells of the epithelium thus increasing epithelial permeability and permitting the allergen to traverse the epithelium. By this means, the allergens may gain access to, and interact with, dendritic antigen presenting cells to produce an allergic response. Cysteine proteinase inhibitors inhibit the cysteine proteinase allergens but not the serine proteinase allergens and so do not completely block tight junction breakdown. Similarly, serine proteinase inhibitors block the effects of serine proteinase allergens but not the cysteine proteinase allergens and so do not completely block tight junction breakdown. Partial inhibition would still allow an allergic response to be produced. Inhibition of both the cysteine and serine proteinase activity of the allergens is necessary to inhibit disruption of the tight junctions completely and thus the generation of an allergic response.

Although the invention is applicable particularly to the prevention and/or treatment of asthma it may be applied to a range of other allergic conditions including rhinitis, allergic conjunctivitis, atopic dermatitis and food allergies.

The treatment and/or prevention of the allergic condition may be effected by means of (i) a formulation (which provides a second aspect of the invention) having cysteine and serine proteinase inhibitory activity; or (ii) a kit (which provides a third aspect of the invention) comprising an inhibitor of cysteine proteinase activity and an inhibitor of serine proteinase activity.

In the formulation of the second aspect of the invention, a single inhibitor compound may provide the required inhibition of serine and cysteine protease activity. However, more usually, and in accordance with a preferred embodiment of the second aspect of the invention, the inhibition of cysteine proteinase activity and serine proteinase activity will be provided by separate inhibitor compounds.

Where separate inhibitory compounds are used as in the kit of the third aspect of the invention, they may be used simultaneously with each other or sequentially.

If necessary more than one type of cysteine proteinase activity and/or more than one type of serine protease activity may be used to provide the required spectrum of activity.

The invention is applicable principally (but not exclusively) to therapeutic treatments.

Therefore according to a fourth aspect of the invention there is provided the use of an inhibitor of cysteine proteinase activity in conjunction with an inhibitor of any serine proteinase activity other than trypsin for the manufacture of a medicament for the prevention or treatment of a condition in which an allergen traverses an epithelial barrier.

According to a fifth aspect of the invention there is provided a method of treating a subject for the prevention or treatment of a condition in which an allergen traverses an epithelial barrier comprising administering to the subject therapeutically effective amount(s) of an inhibitor of cysteine proteinase activity and an inhibitor of serine proteinase activity.

These therapeutic treatments may be effected using the composition of the second aspect of the invention or the kit of the third aspect of the invention.

The fourth and fifth aspects of the invention are particularly applicable to the treatment of asthma and more particularly to the prophylactic treatment thereof. By the term prophylactic treatment we include any treatment applied to prevent, or mitigate the effect of, a subsequent asthmatic attack. The prophylactic treatment may be given, for example, periodically to a person who is known to suffer from asthmatic attacks with a view to preventing, or reducing the frequency of, such attacks. Alternatively the prophylactic treatment may be given on an ad hoc basis to a person who suffers from asthma and who is to be subjected to an environment (e.g. an allergen infected environment) which might make the onset of an asthmatic attack more likely. A further possibility is for the prophylactic treatment to be given to a person who has not developed asthma but who, for one reason or another, is believed to be at risk of doing so.

For the purpose of therapeutic administration, the inhibitory compound(s) will be formulated in a pharmaceutically acceptable excipient for delivery to the lung epithelium. Most preferably the inhibitory compound(s) will be delivered by means of an aerosol as is conventional for anti-asthmatic treatments. We do not however preclude other delivery routes.

The amount of the inhibitory compound(s) to be administered will, of course, be a therapeutically effective dose. The dosage rate will depend on factors such as the weight of the patient to be treated, the severity of the asthmatic condition being treated and the activity of the inhibitors. However typical dosages will be in the range 1 to 1000 microgrammes per day.

Although the invention has so far been described with particular reference to the therapeutic treatment of asthma, our finding that the inhibition of cysteine and serine proteinase activity of house dust mite allergens may be used beyond the field of therapeutic treatment. Thus, for example, it is possible to treat inanimate substrates which contain or potentially contain house dust mite allergens with inhibitors inhibit cysteine and serine proteinase activity, so as to render such substrates hypoallergenic. Examples of such substrates are those which are generally associated with relatively high levels of allergens (e.g. soft furnishings, carpets, bedding etc.).

Examples of inhibitors of cysteine proteinase activity which may be used for any aspect of the invention include L-trans-epoxysuccinyl-leucylamido-(4-guanidino)-butane (E-64) as well as the cysteine proteinase inhibitors disclosed in WO-A-97/04004.

Examples of inhibitors of serine proteinase activity which may be used for any aspect of the invention include 4-(2-aminoethyl)-benzenesulphonyl fluoride hydrochloride (AEBSF).

The invention will be illustrated by the following non-limiting Example (and accompanying Figures) which give results of the Example.

EXAMPLE

Using the methods described in more detail below, the Example demonstrates the effect on epithelial permeability of (i) cysteine and serine proteinase fractions separated from House Dust Mites, and (ii) the fractions specified under (i) in combination with inhibitors of cysteine and serine proteinase activity.

Methods

Cell Culture

Calu-3 and MDCK cells were used as paradigms for examining intercellular junctions of epithelia and their susceptibility to HDM proteinases and potential inhibitors. Both cell lines express tight junctions, zonulae adherentes and desmosomes and are thus acceptable models of cell adhesion mechanisms present in the airway. Calu-3 is an adenocarcinoma cell line derived from a 25-year-old Caucasian male. It has been the subject of relatively few investigations, but is known to express tight barrier properties on the basis of electrophysiological studies (Shen et al., 1994; Haws et al, 1994) and our own immunocytochemical characterization (not shown). Cells were propagated in Eagle's minimum essential medium with Earle's salts (EMEM) supplemented with 10% v/v heat inactivated foetal calf serum (FCS), 2 mM L-glutamine, non-essential amino acids, 10µM sodium pyruvate and containing 50U/ml penicillin and 50µg/ml streptomycin.

Madin-Darby canine kidney (MDCK) epithelial cells were cultured in EMEM containing 50U ml$^{-1}$ penicillin, 50µg ml$^{-1}$ streptomycin, 2 mM L-glutamine, non essential amino acids and 10% v/v heat inactivated FCS. For subculture of both cell types, the cells were rinsed in phosphate-buffered saline (PBS) without calcium and magnesium and then partially digested using a 0.05% (w/v) trypsin and 0.02% (w/v) EDTA solution.

All cultures were propagated at 37° C. in a humidified atmosphere of 5% carbon dioxide in air.

Coating of Transwell™ Inserts with Matrigel

Measurements of mannitol clearance were performed on confluent cell monolayers that had been propagated on 0.4µm pore diameter Costar Transwell™ inserts coated with an ungelled ultra-thin undercoat of Madrigel. Coating was achieved by addition of 250µl aliquots of Matrigel (diluted 1:500 v/v in EMEM) to the interior of the insert followed by ambient incubation for 60 min under aseptic conditions. The solution was then aspirated and the inserts gently washed with medium before the addition of a confluent density of cell suspension.

Cell Treatment Protocols and Measurement of Clearance

Cells (2–5×10$^5$ per cm$^2$ growth area) were plated onto Matrigel-coated inserts. We use the term 'insert' as meaning the filter unit containing the cells and the term 'well' as referring to the cavities of the tissue culture plate. To monitor growth and integrity, inserts were taken at random, washed gently in PBS and stained under subdued illumination with acridine orange and ethidium bromide (1mg ml$^{-1}$ each in PBS). Inserts were examined by fluorescence microscopy and were used only when confluence with high viability was attained.

At confluence, the medium was aspirated from the wells and replaced with serum- and bicarbonate-free EMEM buffered with 20 mM HEPES and containing 2 mM L-glutamine. The medium from the inserts was then gently removed and replaced with 300μl of serum-free EMEM containing [$^{14}$C]-mannitol (1μCi ml$^{-1}$ and 1 mg ml$^{-1}$ unlabelled mannitol in HEPES-buffered medium). The Transwell™ plates were then equilibrated for 30 min at 37° C. on a Luckham R100 orbital shaker. Triplicate 100μl aliquots of the unused labelled mannitol solution were sampled and their radioactivity content determined by liquid scintillation spectrometry (Beckman LS6000IC) following addition of 5 ml Opti-Fluor.

After the equilibration period, the inserts were placed in fresh wells containing 1 ml of serum-free HEPES buffered EMEM and incubated at 37° C. with continuous gentle shaking. The medium from the original wells was retained and its radioactivity content determined after the addition of 10 ml Opti-Fluor. These results were used to determine the tracer concentration at time zero. At timed intervals, 20μl aliquots of the basolateral bathing fluid were removed and the amount of $^{14}$C mannitol quantified as described above for the calculation of clearance volume.

Calculation of Epithelial Permeability

Paracellular permeability of mannitol was determined in accordance with the procedure described in our copending U.K. Patent Application No. 9715058 and was calculated from measurements of clearance volume at defined time points. Clearance estimates were made over 3–5h and were calculated according to the relationship:

$$V_{probe_t} = \sum_{i=1}^{t} \frac{VA_i \cdot \Delta[A]_i}{([L])_i} \quad (1)$$

where:

$V_{probe_t}$ is the clearance volume at each time point

VAi is the abluminal volume at each time point

Δ[A]i is the increase in tracer concentration between time points

[L]i is the luminal tracer concentration at each time point

Under conditions where diffusion is the sole means of transepithelial movement of the solute, $dV_{probe}/dt$ approximates closely to the permeability-surface area product thus allowing estimation of the permeability of mannitol in the composite system of cells, filter, unstirred layers and protein coating ($P_t$). Epithelial permeability can be calculated from the measured variable by considering the Matrigel-coated filter and unstirred layers as a system of series permeabilities. Thus:

$$\frac{1}{P_t} = \frac{1}{P_1} + \frac{1}{P_2} + \frac{1}{P_3} \quad (2)$$

and $$\frac{1}{P_4} = \frac{1}{P_2} + \frac{1}{P_3} \quad (3)$$

where $P_t$ is the composite permeability of the system $P_1$ is the component due to the epithelial cells alone $P_2$ is the component due to the filter without Matrigel $P_3$ is the unstirred layer component $P_4$ is the permeability of the filter with the Matrigel coating In pure diffusion systems $$P_3 = \frac{D}{\delta} \quad (4)$$

where D is the free diffusion coefficient of mannitol δ is the summed thickness of unstirred layers Unstirred layer thicknesses are independent of membrane permeability under ideal conditions thus $P_3$ in equations (3) and (4) are identical. Subtracting equations (2) and (3) thus permits the calculation of the permeability of the epithelial monolayer (5).

$$\frac{1}{P_l} = \frac{1}{P_t} - \frac{1}{P_4} \quad (5)$$

Analysis of variance was performed after log transformation of the permeability data and probability values for the different treatments assigned using the least significant difference test. Data are presented as the geometric mean values with indicated standard errors of n experimental observations. Probability levels of $P<0.05$ were considered statistically significant.

Preparation of Proteinase Fractions from HDM Culture Medium

HDM proteinase allergens have not yet been prepared in catalytically competent form by recombinant cellular expression of the mature enzyme protein. For convenience, and to enable future large scale screening of potential inhibitors in the absence of catalytically active recombinant proteins, we sought to separate the cysteine and serine proteinase activity by simple biochemical fractionation of spent medium in which HDM had been grown. During culture the HDM release allergens into the medium resulting in the accumulation of proteins suitable for purification. Spent medium from cultures of D. pteronyssinus (Commonwealth Serum Laboratory, Parkville, Australia) was dissolved in 5 volumes of phosphate buffered saline and then centrifuged at 48,400×g and 4° C. for 20 min. Ammonium sulphate was added gradually to the stirred supernatant at 4° C. to achieve a 50% saturated solution. After centrifugation (48,400×g, 20 min, 4° C.) the pellet, found by enzymatic assay to be enriched in cysteine proteinase activity, was redissolved in a minimum volume of distilled water. Ammonium sulphate was added to the supernatant from the first cut to achieve 80% saturation. The pellet resulting from further centrifugation, found to be enriched in serine proteinase activity, was resuspended in a minimum volume of distilled water. The cysteine (50% precipitate) and serine proteinase (50–80% precipitate) fractions were separately dialysed against distilled water overnight and then lyophilized prior to reconstitution in EMEM. Protein content of the extracts was measured using the Coomassie Blue technique with serum albumin as standard (Smith et al, 1985). Proteinase activity was measured using the Azocoll degradation assay as described elsewhere (Herbert et al., 1995; Chavira et al., 1984). Extracts were also assayed for the presence of endotoxin using the Limulus amebocyte lysis assay (Endotect™, ICN Biomedicals, Thame, Oxfordshire). In all cases the levels of endotoxin were below the limit of assay detection (<0.06ng ml$^{-1}$).

Immunoblotting of HDM Proteinase Fractions

Proteinase fractions were separated by SDS-PAGE and transferred electrophoretically to nitrocellulose membranes. Non-specific protein binding was blocked with 5% w/v non-fat milk and 0.1% v/v Tween-20 in Tris-buffered saline (TBS) followed by incubation with mAb 5H8 (anti-Der p 1) diluted in TBS containing 2% w/v bovine serum albumin and 0.1% v/v Tween-20. Detection was by enhanced chemiluminscence technique (Amersham International, Buckinghamshire).

Cells were plated on 60×15 mm petri dishes and grown for 2–4 days in serum-containing EMEM under tissue culture conditions in a 5% $CO_2$ atmosphere. Cells were then exposed to treatments in serum-free EMEM containing 20 mM HEPES whilst under aerobic incubation at 37° C. At defined time points, cells were harvested with a scraper and pooled with detached cells in the supernatant. Cells were centrifuged at 550×g for 5 min and their DNA extracted (Nucleon II, Scotlab, Coatbridge, Stratchclyde). The extracted DNA was resuspended in 100μl TE buffer (10 mM Tris-HCL and 1 mM $Na_2EDTA$) overnight at room temperature and its purity determined spectrophotometrically. Equal amounts of DNA were applied in 4:1 ratio with sample buffer (0.25% bromophenol blue and 40% w/v sucrose in water) to each lane of 2% (w/v) agarose gels and electrophoresis performed at 50V for 2–3h in TAE buffer (0.04M Tris-acetate and 0.001M EDTA). Bands of DNA in the gels (which had ethidium bromide incorporated into them) were visualized by ultra-violet light.

The redistribution of phosphatidylserine into the outer layer of cell membranes which occurs during the initiation of apoptosis was studied using annexin V staining. This was performed in 60×15 mm petri dishes which had been modified by drilling a 1 cm diameter hole into the base of each dish and covering the external face of this with a glass coverslip secured in place by Sylgard (Dow Corning, Midland, Mich., USA). A polyamide ring was mounted by means of cyanoacrylate adhesive onto the inner face of the dish to create a glass-bottomed well which was then coated with an ultrathin layer of Matrigel. Cells (3×10$^4$) were plated into each well and allowed to grow for 2–3 days, after which they were exposed to the desired experimental treatment. Following this, cells were rinsed in PBS and then in 200 ml binding buffer prior to addition of annexin V-FITC (AV) and propidium iodide (PI) under subdued lighting conditions. After incubation for 15 min the cells were rinsed with binding buffer and examined by fluorescence microscopy using blue and green excitation filter sets (Zeiss Axiovert 10 with oil immersion Fluar objectives). Using this technique, cells in early apoptosis stain green because FITC-conjugated annexin V binds to phosphatidylserine which has become reorientated into the outer leaflet of the cell membrane (Fadok et al., 1992; Koopman et al., 1994; Vermes et al., 1995; Homburg et al., 1995). Dead cells also show red staining with PI because increasing permeability of the nuclear membrane allows it to bind to nucleic acids. Photographic documentation was made using a Contax 167MT camera and Kodak TMAX 400 film for black and white prints or Ektachrome 160T for colour reversal images.

LDH activity was measured using pyruvic acid as substrate and monitoring spectrophotometrically the formation of a phenylhydrazone derivative from lactic acid. MDCK or Calu-3 cells were seeded onto 12-well plates and grown to confluency. Cell monolayers were exposed for 18 h to either control treatments (serum- and phenol red-free EMEM. with 0.6 mM dithiothreitol in the case of the control for the cysteine proteinase fraction) or the HDM proteinase fractions diluted in the same medium (with 0.6 mM dithiothreitol present in the cysteine proteinase fraction). At the end of the experiment the incubation medium was harvested and centrifuged at room temperature to sediment any cells which had detached from the wells during treatment. The first supernatant fraction was assayed directly for LDH activity, whereas the pellet formed by any detached cells was subjected to hypotonic lysis with distilled water (5 min at room temperature) prior to brief centrifugation to remove cellular debris. The resulting second supernatant was then assayed for LDH activity. Cells which had remained adherent to the wells during treatment were lysed as described above and LDH activity measured. Because no significant detachment occurred during treatment with control media, total cellular LDH activity was defined as that present in the lysate from adherent cells treated with serum- and phenol red free EMEM alone.

Immunocytochemical Visualization of the Effects of Inhibitors on Proteinase-mediated Cleavage of Intercellular Junctions To study the effects of proteinases and inhibitors on intercellular junctions, MDCK cells were cultured on coverslips and treated with the appropriate proteinase and/or inhibitor for the desired time period. The cells were fixed in ice-cold methanol before binding of rat anti-ZO-1 (mAb R40.76) (Stevenson et al., 1986; Anderson et al., 1988) and mouse anti-desmoplakin (mAb 11-5F) (Parrish et al., 1987). Indirect fluorescent antibody staining was performed using FITC- and TRITC-conjugated second antibodies. Microscopy was carried out using a Zeiss Axiovert microscope with x40 magnification oil immersion Fluar objective. Specimens were illuminated using excitation and emission filter sets for FITC and TRITC. Cells were photographed as described above.

Materials

All media and cell culture reagents were purchased from ICN Biomedicals Ltd (Thame, Oxfordshire). except where stated. HBSS was obtained from GibcoBRL, Life Technologies Ltd (Paisley). Mannitol and Triton X-100 were obtained from Sigma Aldrich Ltd (Poole, Dorset) and heat inactivated foetal calf serum was from Labtech International Ltd (Uckfield, East Sussex). Matrigel was obtained from Universal Biologicals, London. Mannitol clearance measurements were made in 12 mm diameter Transwells with 0.4μm membrane pore size and 10μm membrane thickness (Costar UK Ltd, High Wycombe, Buckinghamshire). D-[$^{14}$C]-mannitol was obtained from NEN Du Pont Research Products (Stevenage, Hertfordshire), and the Opti-Fluor scintillant and the scintillation vials were from Canberra Packard Ltd (Pangbourne, Berkshire). MDCK cells were grown from stock in our laboratory. Calu-3 cells were originally obtained from the American Type Culture Collection (Rockville, Md., USA) and expanded by serial passage to create a local bank of cryopreserved cells. Cells were cultured in Falcon 75 cm$^2$ cell culture flasks (Marathon Laboratory Supplies, London). Costar multiwell tissue culture plates or Transwell inserts according to the nature of the experiment. Agarose (molecular grade) was from Promega (Southampton, Hampshire). Assay kits for LDH measurement were purchased from Sigma; Apoalert kits were purchased from Cambridge Bioscience. Acridine orange, ethidium bromide and all other general laboratory reagents were obtained from BDH (Poole, Dorset). Compound E-64 (L-trans-epoxysuccinyl-leucylamido-(4-guanidino)-butane, an inhibitor of cysteine proteinases, was obtained from Sigma. Concentrated aqueous stock solutions were stored frozen until required. The serine proteinase inhibitor 4-(2-aminoethyl)-benzenesulphonyl fluoride hydrochloride (AEBSF) was obtained from Pentapharm, Basle, Switzerland. The matrix metalloproteinase (MMP) inhibitor BB-250 ([4-(N-hydroxyamino)-2R-isobutyl-3S-(thiophen-2-yl-sulphonylmethyl)succinyl]-L-phenylalanine-N-methylamide) was provided by British Biotech Pharmaceuticals Ltd. All inhibitors were made as concentrated stock solutions in dry $Me_2SO$ and diluted as required with medium for use in experiments. Appropriate controls for the $Me_2SO$ vehicle were incorporated into experiments as required. Monoclonal antibody R40.76 reactive against ZO-1 was generously provided by Dr Bruce Stevenson, University of Alberta. Monoclonal Der p 1 antibody 5H8 was a kind gift of Dr Martin Chapman, University of Virginia, USA.

Results

Fractionation of Spent Mite Medium

Spent mite medium was separated into two fractions by ammonium sulphate precipitation. The fraction yielded by precipitation with 50% ammonium sulphate consisted of major protein bands at ~22 KDa and 38 KDa (FIG. 1a, lane 2). Tests of enzyme degradation using chromogenic substrates showed that the catalytic activity of the 50% precipitate was inhibitable by E-64 (not shown). Immunoblot analysis of the 50% precipitate using mAb 5H8 raised against Der p 1 revealed the presence of a major band with an apparent mass of ~22 KDa and a minor band at 38 KDa (FIG. 1b, lane 2). In the SDS-PAGE and immunoblotting analyses the the cysteine proteinase fraction behaved identically to Der p 1 purified by a combination of immunoaffinity chromatography, gel filtration and isoelectric focussing (compare lanes 1 and 2 in panels a,b of FIG. 1). Comparison of lanes 2 and 3 of the immunoblot shown in FIG. 1b demonstrates that the 5H8 mAb also reacted with an additional range of proteins present in the 50–80% ammonium sulphate precipitate. In the absence of reducing agent the 50–80% ammonium sulphate precipitate fraction exhibited high catalytic activity which was attenuated by inhibitors of archetypal serine proteinases (not shown). For convenience, in this manuscript the 50% precipitate is subsequently referred to as the cysteine proteinase fraction and the 50–80% precipitate as the serine proteinase fraction.

Effects of HDM Proteinase Fractions on Epithelial Permeability

Figure 2:
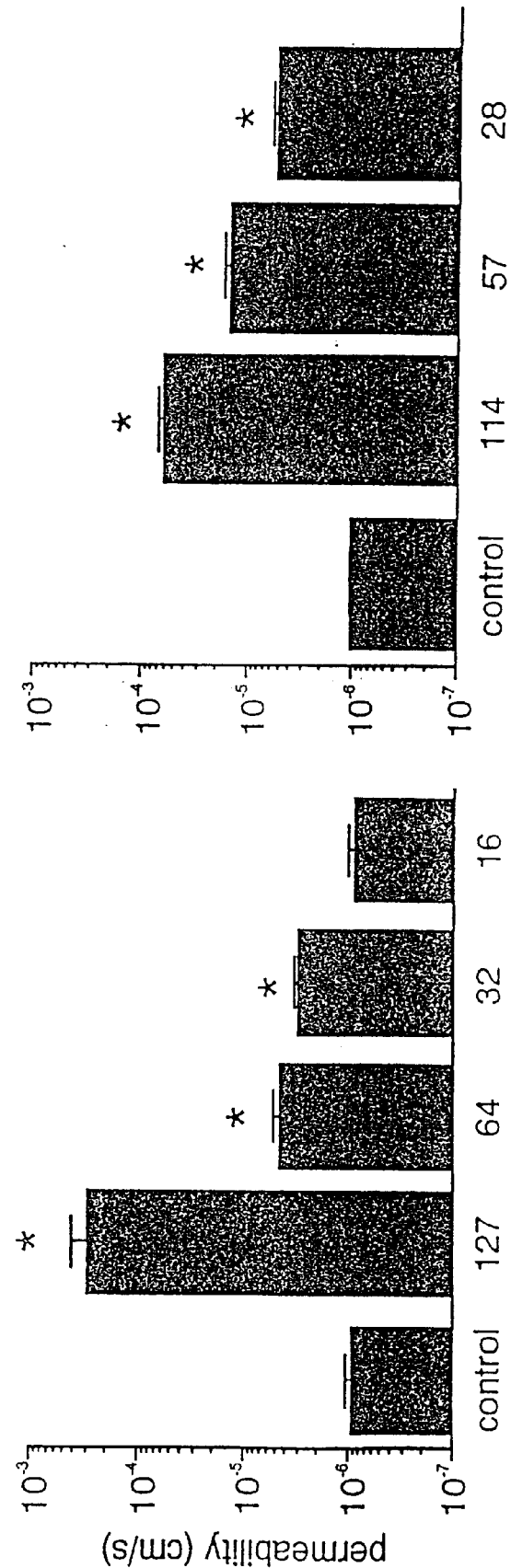

Under the control conditions used in these experiments both MDCK and Calu-3 epithelial cells lines form tight monolayers with mannitol permeabilities in the range $0.7–1.2 \times 10^{-6}$ cm $s^{-1}$. Exposure of either MDCK or Calu-3 cell monolayers to the serine proteinase fraction produced a concentration-related change in permeability (FIG. 2). The concentration-dependency of the cysteine proteinase fraction was not tested in this particular series of experiments, but the effects of pure cysteine proteinase allergen Der p 1 have been previously demonstrated by us in similar in vitro models (Herbert et al., 1990; 1995).

Figure 3:
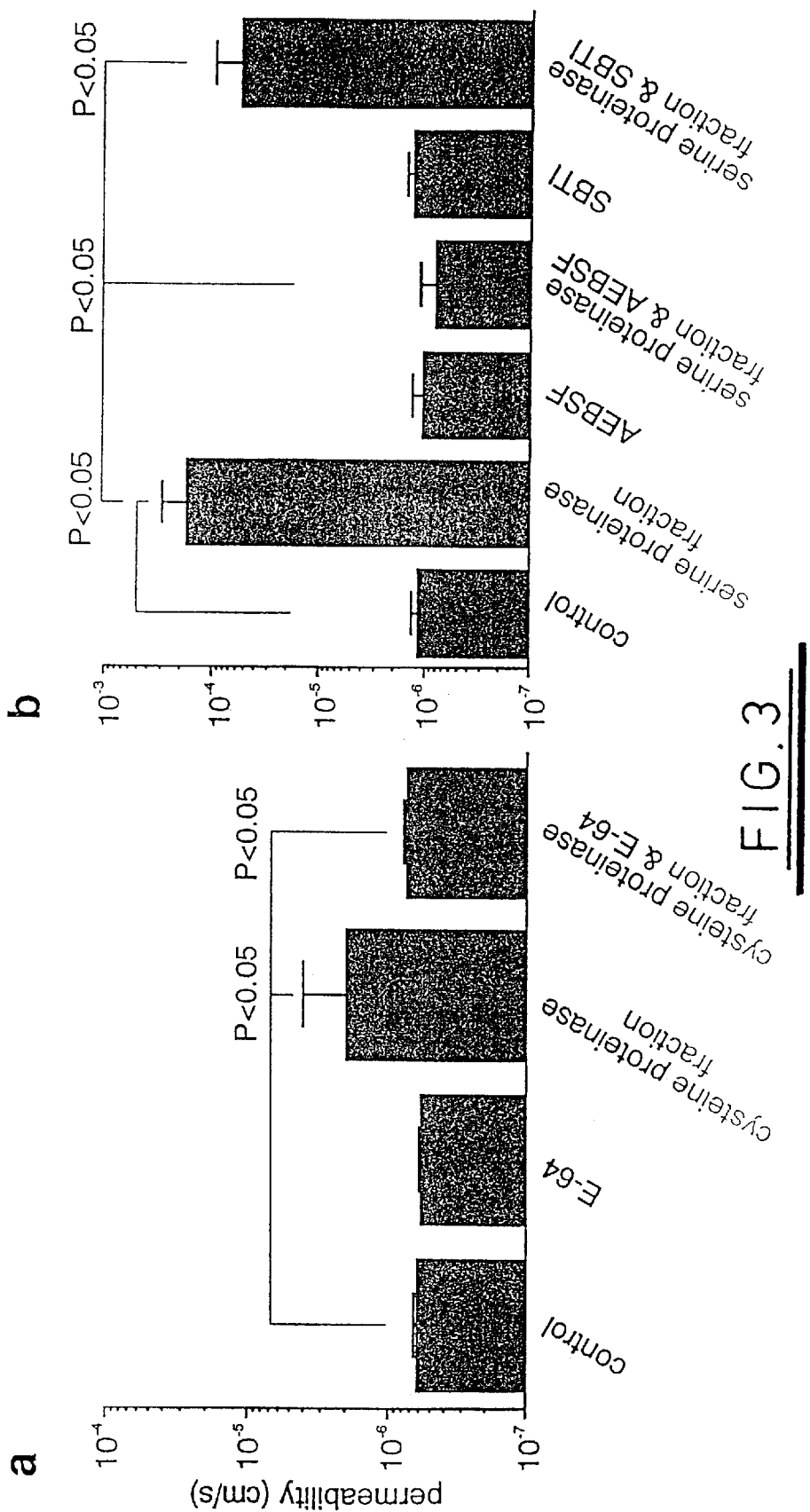

The effects of the cysteine proteinase fraction in MDCK cell monolayers were attenuated by the cysteine proteinase inhibitor E-64 (FIG. 3a). E-64 had no observable effect on the intrinsic permeability properties of the cell monolayer (FIG. 3a). The serine proteinase inhibitors AEBSF and, less effectively, SBTI both inhibited the action of the serine proteinase fraction in MDCK cells (FIG. 3b). Neither inhibitor per se exerted any observable effect on epithelial permeability (FIG. 3b). The inhibitors were also effective when tested at the same concentration in Calu-3 cell monolayers. Calu-3 cell monolayers treated with the cysteine proteinase fraction had a mannitol permeability of $(8.44 \pm 0.43) \times 10^{-6}$ cm $s^{-1}$ which was reduced to $(4.84 \pm 0.32) \times 10^{-6}$ cm $s^{-1}$ by E-64 ($P<0.05$, n=5). Calu-3 cell monolayers treated with the serine proteinase fraction had a mannitol permeability of $(18.1 \pm 0.02) \times 10^{-6}$ cm $s^{-1}$ which was reduced to $(10.20 \pm 0.01) \times 10{-6}$ cm $s^{-1}$ by AEBSF ($P<0.05$, n=5).

Figure 4:
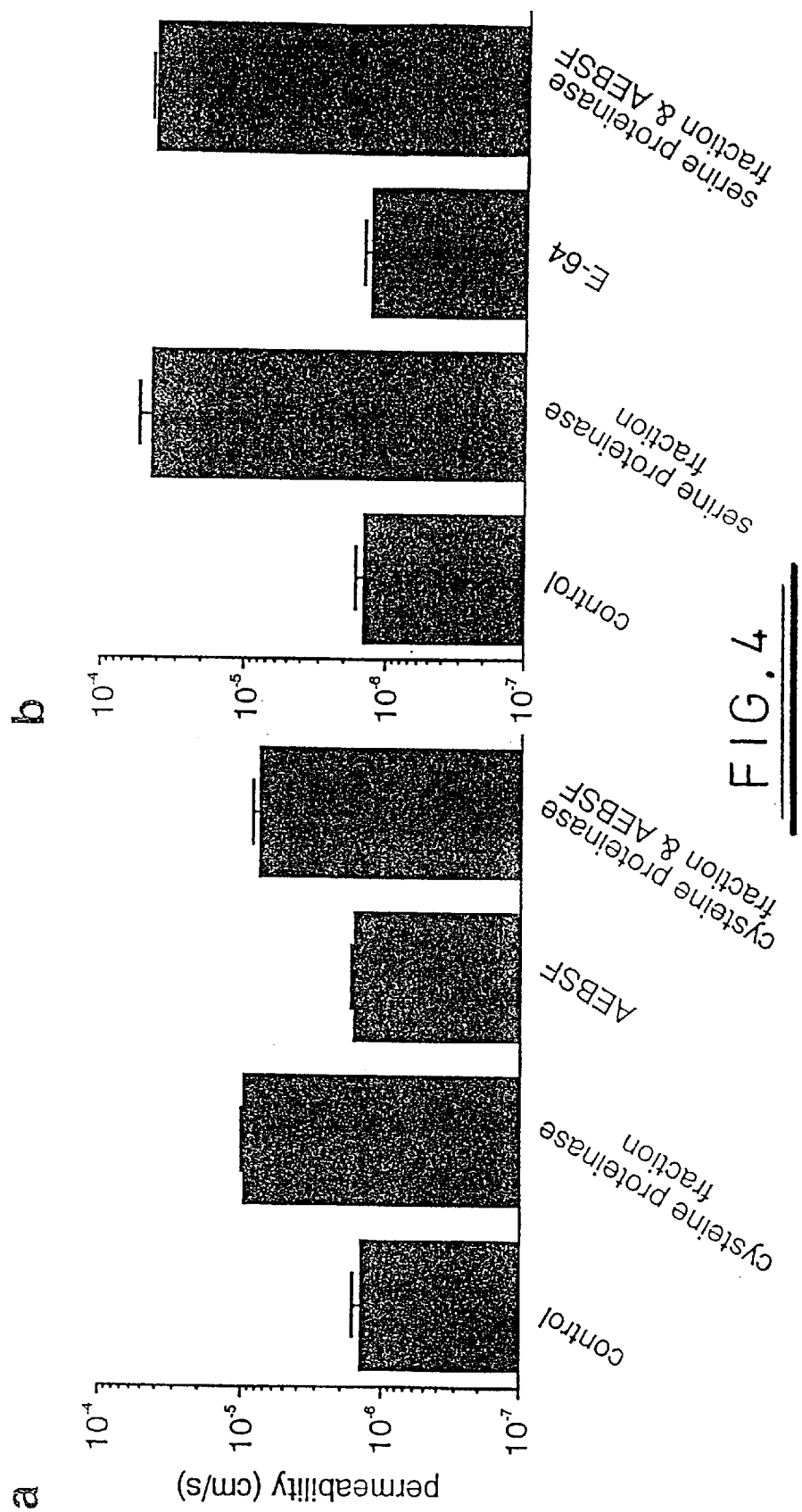

The class-specific proteinase inhibitors were only effective against the cognate enzyme fractions derived from the HDM cultures. FIG. 4 shows that AEBSF, at a concentration which ablated the effects of the serine proteinase fraction, failed to inhibit the action the cysteine proteinase fraction on Calu-3 cell monolayers. Conversely, E-64 did not inhibit the permeability change caused by the serine proteinase fraction (FIG. 4).

Figure 5:
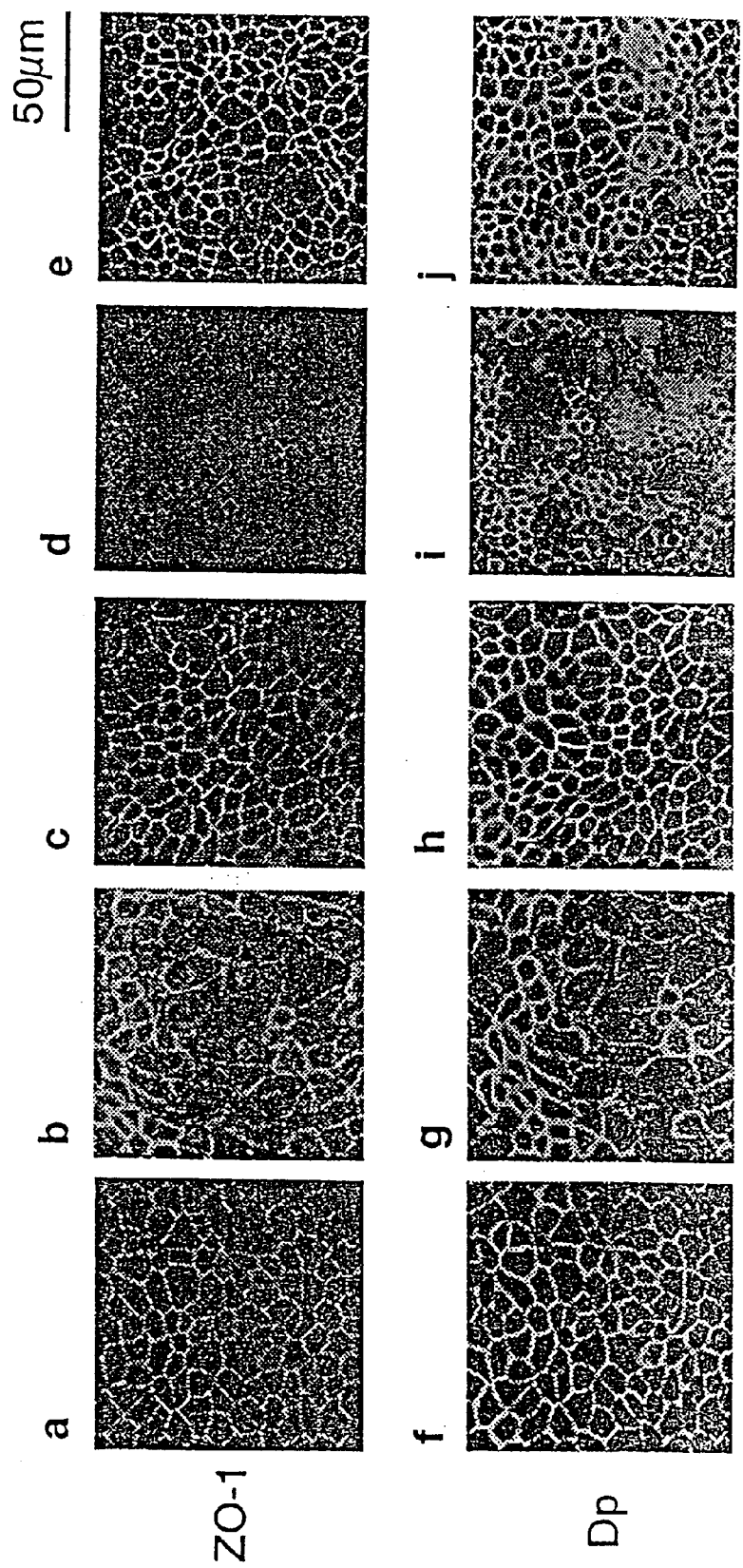

FIG. 5 shows that treatment of MDCK cell monolayers with either the cysteine or serine proteinase fractions produced a disruption of the normally contiguous peripheral staining pattern of the TJ protein ZO-1 and of the punctate staining of desmoplakin. Addition of E-64 to the cysteine proteinase fraction or AEBSF to the serine proteinase fraction inhibited the proteinase-dependent changes (FIG. 5).

HDM Proteinases Induce Cell Death in Epithelia

Figure 6:
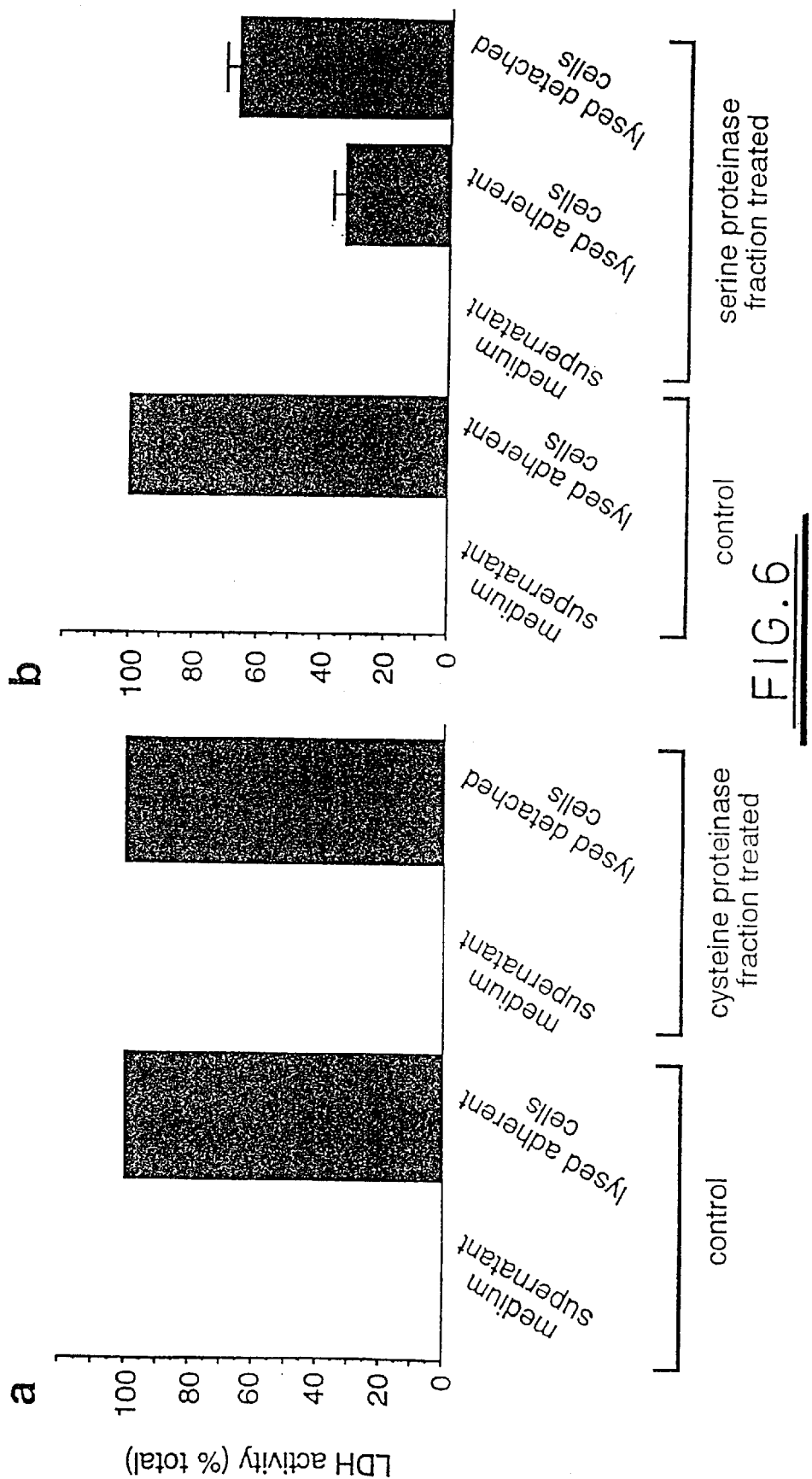
Figure 6:
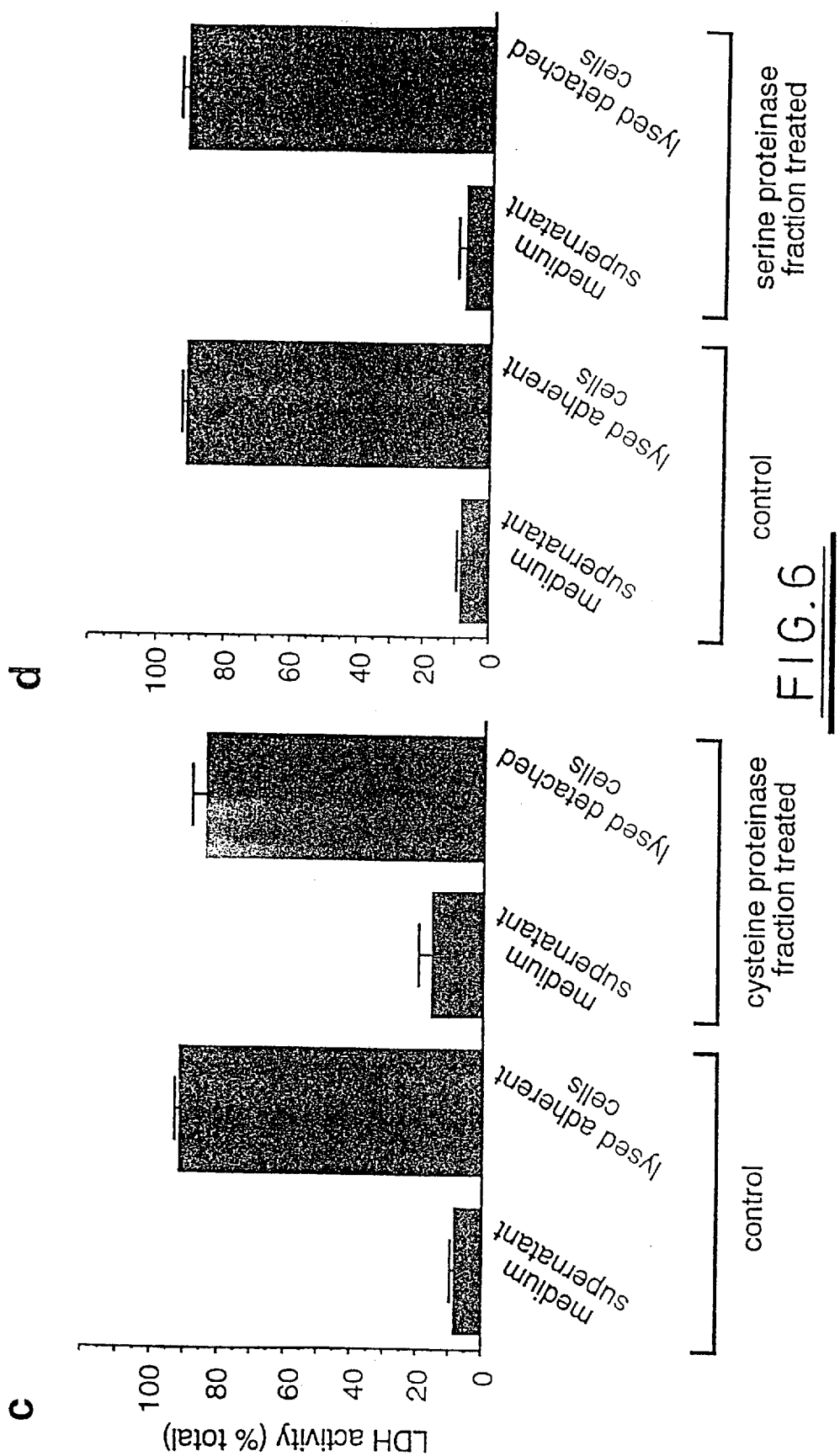

Control incubation of MDCK or Calu-3 cell monolayers for 18 h in serum-free EMEM produced negligible release of LDH until they were subjected to hypotonic lysis at the end of the experiment (FIG. 6). Treatment of monolayers of either cell type with the cysteine and serine proteinase fractions also failed to release significant amounts of LDH into the incubation medium (FIG. 6), despite the fact that some cells detached from the matrix substratum during the experiment. Lysis of the detached cells and the adherent cells resulted in the recovery of LDH equivalent in amount to that found in untreated cell lysates (FIG. 6).

Figure 7:
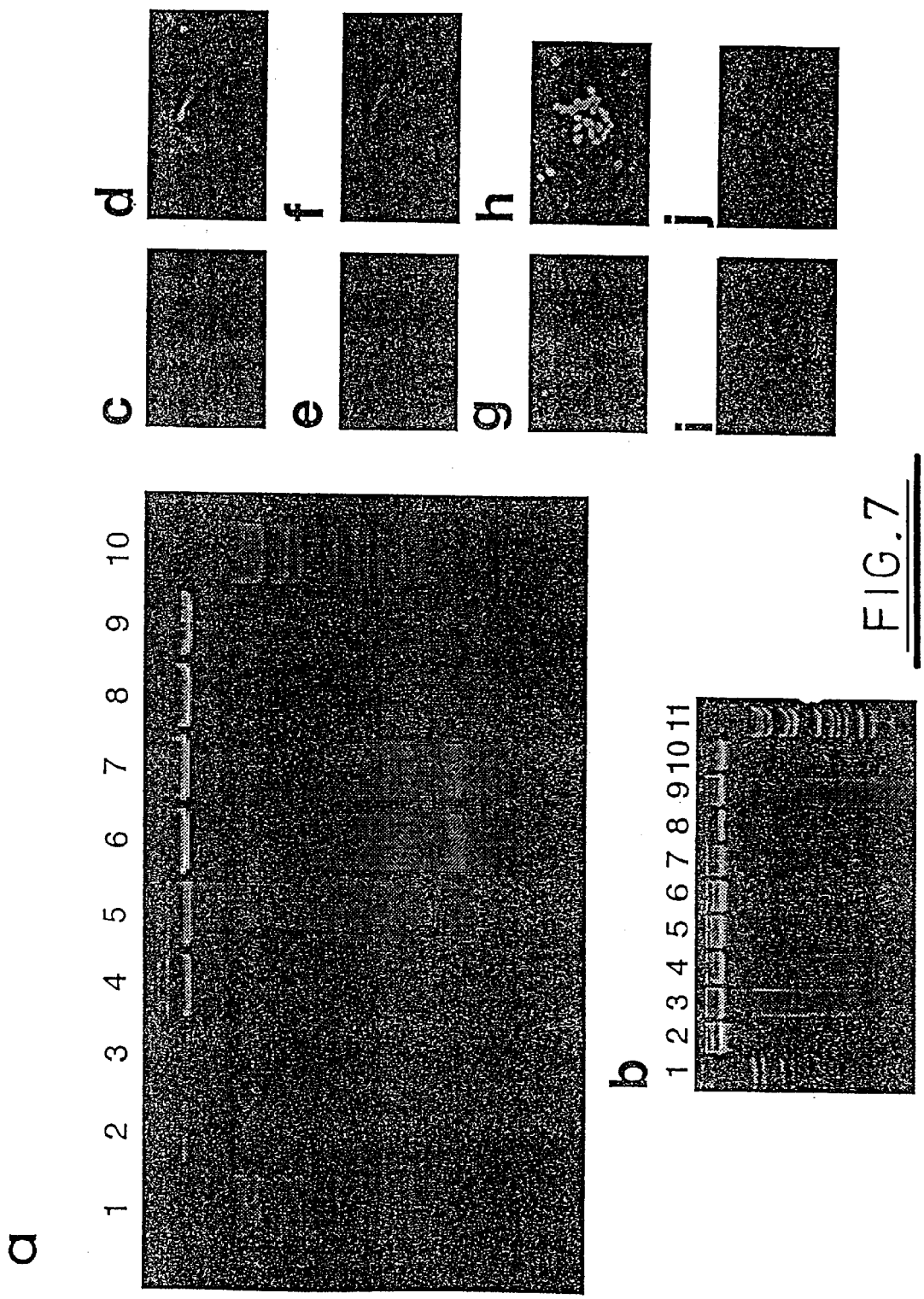

Cell death was also studied by examining DNA fragmentation and studying the staining of cells with AV and PI. FIG. 7a,b shows evidence of DNA fragmentation in MDCK and Calu-3 cells following treatment with HDM proteinases under conditions that result in an increase in permeability of epithelial monolayers. The effects of both HDM proteinase fractions were attenuated by the matrix metalloproteinase inhibitor BB-250 (FIG. 7b). E-64 inhibited the effects of the cysteine proteinase fraction, but not the serine proteinase fraction (FIG. 7b). FIG. 7 also shows that treatment of MDCK or Calu-3 cells with the serine proteinase fraction resulted in some cells within monolayers binding annexin V alone ($AV^+PI^-$), indicative of early apoptosis in these cells, and others which stained with both annexin V and PI ($AV^+PI^+$) indicating cell death (see FIG. 7d,f,h,j). The spatial distribution of $AV^+PI^-$ early apoptotic cells and $AV^+PI^+$ dead cells was clustered around regions where there was clear disruption of cell adhesion (eg see FIG. 7d,f).

Discussion

HDM faecal pellet proteins are a major cause of allergic asthma (Tovey et al., 1981) and in large part underlie the increasing prevalence of the disease (Dowse et al., 1985). In this study we have shown that proteinases from D. pteronyssinus faecal pellets exert potent biological effects on epithelial cells. The HDM proteinases were fractionated by ammonium sulphate precipitation into cysteine and serine classes. Both precipitates had similar effects in the experimental systems investigated. They produced an increase in permeability of epithelial monolayers, caused cleavage of lateral cell adhesion, and detached cells from the biomatrix substratum. Cleavage and detachment of cells was not associated with gross release of LDH, but evidence was found of early apoptosis and outright cell death with nuclear rupture. Inspection of cells stained with AV and PI revealed that staining was localized to areas of cell disruption/detachment. We further demonstrated that cell death could be attenuated by proteinase inhibitors.

Ammonium sulphate precipitation proved to be an effective means of separating the major classes of proteinase activity in the spent HDM culture medium. The fraction precipitated by 50% ammonium sulphate had cysteine proteinase activity and its permeability promoting effect on epithelial cell monolayers was inhibited by E-64 but not the serine proteinase inhibitor AEBSF. SDS-PAGE and immunoblot analysis with mAb 5H8 raised against the HDM allergen Der p1 (a cysteine proteinase) revealed the presence of bands with apparent molcular masses of ~22 KDa and ~38 KDa in this fraction. In contrast, the fraction precipitated by 50–80% saturated ammonium sulphate had serine proteinase activity and its effects on epithelial cells were inhibited by AEBSF, and to a lesser degree SBTI, but not at all by E-64. We conclude from the studies with inhibitors that there was a minimal functional carry over of the cysteine proteinase allergen into this fraction. SDS-PAGE and immunoblot analysis revealed the presence of several protein bands in the serine proteinase fraction, some of which were recognized by mAb 5H8 (eg approximate apparent masses 22, 26, 28, 29 and 38 KDa). The mAb 5H8 is widely used to purify and quantify Der p 1, but its specificity has recently been called into question (Cambra & Berrens, 1996). Thus, an incidental finding from our study is cause for further concern regarding the specificity of this antibody. The protein bands detected in the 50–80% ammonium sulphate precipitate are consistent with the presence of the serine proteinase allergens Der p 3, Der p 6 and Der p 9. On the basis of these observations we suggest that ammonium sulphate fractionation of HDM culture extracts provides a simple and effective means to study the biological effects of HDM proteinase allergens and also to identify novel inhibitors of their effects.

We have previously shown that highly purified Der p 1 allergen induces an increase in the transepithelial flux of serum albumin in the airway mucosa, causes disruption of epithelial architecture and detaches MDCK cells from natural biopolymer substrata (Herbert et al., 1990; 1995). We also demonstrated that these effects of Der p 1 were a result of its cysteine proteinase activity because they were sensitive to inhibition by E-64, a relatively specific inhibitor of most cysteine proteinases (Barrett et al., 1982; Shaw, 1994; Herbert et al., 1995). Although comparisons of amino acid sequence predict that Der p1 is a putative cysteine proteinase (Chua et al., 1988; 1993; Stewart, 1994; Topham et al., 1994; Robinson et al., 1997), others have suggested that it might act as a bifunctional cysteine-serine proteinase because its activity has also been reported to be inhibited by APMSF, an inhibitor of serine proteinases (Hewitt et al., 1995, 1997). If correct, this proposed bifunctionality would have potentially important implications for the design of specific inhibitors of Der p 1. However, in the present study we argue against the functional significance of claimed bifunctionality by showing (i) that the cysteine proteinase fraction derived from HDM cultures could not be inhibited by concentrations of AEBSF that significantly inhibited the activity of the serine proteinase fraction, and (ii) the serine proteinase fraction being resistant to inhibition by E-64 at concentrations at which this inhibitor blocks cysteine proteinase activity. Other evidence against Der p 1 being a mixed cysteine-serine proteinase has also been presented recently (Chambers et al., 1997).

The permselectivity of the bronchial epithelium to hydrophilic solutes is governed by TJs which are expressed circumferentially at the apical pole of each cell (Schneeberger & Lynch, 1992). Contiguous expression of the TJ proteins of one cell and their close opposition with TJ proteins on adjacent cells is thought to result in the epithelium being able to develop its tight properties (Anderson & Van Itallie, 1995; Robinson, 1995). Disruption of the interaction of the TJ proteins between cells, for example by the formation of discontinuities in their perijunctional localization, is associated with failure of epithelial barriers (Howarth et al., 1994; Zhong et al., 1994; Stuart et al., 1994 Stuart & Nigam, 1995). Both fractions of HDM proteinase used in this study caused breakdown of TJs as assessed by loss of perijunctional staining of ZO-1. Some disruption of desmosomes was also observed. The breakdown of TJs resulted in an increased permeability of epithelial monolayers, and eventually physical detachment of cells from the substratum occurred. The loss of ZO-1 from TJ and desmoplakin from desmosomes was dependent upon exogenous proteinase activity because the process was attenuated by E-64 (in the case of the cysteine proteinase fraction) and AEBSF (in the case of the serine proteinase fraction). Although ZO-1 and desmoplakin are intracellular proteins, and thus unlikely to be degraded by exogenous proteinases, their breakdown is explicable as a consequence of disruption of other, membrane-exposed, components of TJ and desmosomes. A similar mechanism has been invoked to account for changes in other intracellular proteins following cleavage of intercellular contacts (Volk et al., 1990).

The effects of the proteinases did not result in significant release of LDH by the cells. However, treatment with either of the proteinase fractions resulted in some cells exhibiting signs of early apoptosis ($AV^+PI^-$) or outright cell death ($AV^+PI^+$). Cells may enter apoptosis by multiple mechanisms (reviewed in Hale et al., 1996) including changes in homotypic and heterotypic cell adhesion and cell-matrix attachment (Boudreau et al., 1995,1996; Mahida et al., 1996; Frisch & Francis, 1994). An early signalling event in programmed cell death is disruption of phospholipid binding cytoskeletal proteins which leads to the transmembrane redistribution of phosphatidylserine (Martin et al., 1995$a,b$). The framework of cytoskeletal proteins is normally stabilized and restrained by direct interaction with protein components of intercellular junctions (Furuse et al., 1994; Anderson & Van Itallie, 1995) which suggests that proteolysis of intercellular adhesions, especially TJ, could be the critical event in orchestrating the cellular response to proteinase allergens. The ability of E-64 to inhibit the action of the cysteine but not serine proteinase fraction suggests that E-64 acted at a proximal step in the process leading to permeability changes and apoptosis, rather than by inhibiting a distal proteolytic step in a transduction mechanism. Furthermore, intracellular signalling proteinases of the ICE/ced-3 caspase family that are activated inter alia by Fas/APO-1 ligation in apoptosis (Los et al., 1995; Mariani et al., 1995; Kayagaki et al., 1995; Tanaka et al., 1996) have an unusual inhibitor profile in being insensitive to E-64. In contrast, the inhibitory action of BB-250 may occur through prevention of Fas ligand release (Mariani et al., 1995; Kayagaki et al., 1995).

Lung sensitization to airborne allergens such as those of HDM is central to the pathogenesis of allergic asthma. The lung epithelium forms a barrier that foreign proteins must cross before they can cause allergic sensitization, but the mechanism by which allergens cross the epithelial barrier is poorly understood (Robinson et al., 1997). The enzymatic nature of proteins derived from HDM feacal pellets provides one expalantion of the mechanism by which allergens encounter the immune system. By causing focal disruption of tight junctions, and ultimately the loss of a moribund cell, HDM proteinases would be able to increase the paracellular permeation of allergens to antigen presenting cells. It is noteworthy that the localized trauma and cell death produced by proteolytic cleavage of intercellular junctions may also fulfill some conditions of the 'danger model' of adaptive immunological response and thus explain why antibody-directed responses are evoked (Matzinger, 1994; Ridge et al., 1996). In further support of this view recent evidence has suggested that when apoptosis (often considered to be an immunologically 'silent' form of cell death) occurs in the presence of tissue injury the resulting combined stimulus is actually threatening to antigen presenting cells (Boockvar et al., 1994; Casciola-Rosen et al., 1994; Ibrahim et al., 1996).

In summary these results show that HDM proteinases have effects on epithelial cells which are likely to promote allergic sensitization. The ability of specific inhibitors to interfere with epithelial cell responses to proteinase allergens provides a rationale for the prevention and/or treatment of allergic conditions.

References

ANDERSON, J. M., STEVENSON, B. R., JESAITIS, L. A., GOODENOUGH, D. A. & MOOSEKER, M. S. (1988). Characterization of ZO-1, a protein component of the tight junction mouse liver and Madin-Darby canine kidney cells. *J Cell Biol.*, 106, 1141–1149.

ANDERSON, J. M. & VAN ITALLIE, C. M. (1995). Tight junctions and the molecular basis for regulation of paracellular permeability. *Am. J. Physiol.*, 269, G467–475.

BARRETT, A. J., KEMBHAVI, A. A., BROWN, M. A., KIRSCHKE, H., KNIGHT, C. G., TAMAI, M. & HANADA, K. (1982). L-trans-Epoxysuccinyl-leucylamido(4-guanidino)butane (E-64) and its analogues as inhibitors of cysteine proteinases including cathepsins B, H and L. *Biochem. J.*, 201, 189–198.

BOOCKVAR, K. S., GRANGER D. L., POSTON, R. M., MAYBODI, M., WASHINGTON M. K., HIBBS, J. B. jr. & KURLANDER, R. L. (1994). Nitric oxide produced during murine listeriosis is protective. *Infect. Immun.*, 62, 1089–1100.

BOUDREAU, N., WERB, Z. & BISSELL, M. J. (1996). Suppression of apoptosis by basement membrane requires three-dimensional tissue organization and withdrawal from the cell cycle. *Proc. Natl. Acad. Sci. USA*, 93, 3509–3513.

BOUDREAU, N., SYMPSON, C. J., WERB, Z. & BISSELL, M. J. (1995). Suppression of ICE and apoptosis in mammary epithelial cells by extracellular matrix. *Science*, 267, 891–893.

CASCIOLA-ROSEN, L. A., ANHALT, G. & ROSEN, A. (1994). Autoantigens targeted in systemic lupus erythematosus are clustered in two populations of surface structures on apoptotic keratinocytes. *J. Exp. Med.*, 179, 1317–1330.

CHAMBERS, L., SUNEAL, K., SREEDHARAN, S. D., KALSHEKER, N. & BROCKLEHURST, K. (1997). Is the dust mite allergen Der p I a cysteine proteinase? *Biochem. Soc. Trans.*, 25, 85S.

CHAVIRA, R., BURNETT, T. J. JR. & HAGEMAN, J. H. (1984). Assaying proteinases with Azocoll. *Anal. Biochem.*, 136, 446–450.

CHUA, K. Y., STEWART, G. A. & THOMAS, W. R., SIMPSON, R. J., DILWORTH, R. J., PLOZZA. T. M. & TURNER K. J. (1988). Sequence analysis of cDNA coding for a major house dust mite allergen, Der p I. Homology with cysteine proteases. *J. Exp. Med.*, 167, 175–182.

CHUA, K. Y., KEHAL, P. K. & THOMAS, W. R. (1993). Sequence polymorphisms of cDNA clones encoding the mite allergen Der p I. *Int. Arch. Allergy Immunol.*, 101, 364–368.

COZENS, A. L., YEZZI, M. J., KUNZELMAN, K., OHRUI, T., ENG, K., FINKBEINER, W. E., WIDDICOMBE, J. H. & GRUENERT, D. C. (1994). CFTR expression and chloride secretion in polarized immortal human bronchial epithelial cells. *Am. J. Respir. Cell Mol. Biol.*, 10, 38–47.

DOWSE, G. K., TURNER, K. J., STEWART, G. A., ALPERS, M. P. & WOOLCOCK, A. J. (1985). The association between Dermatophagoides mites and the increasing prevalence of asthma in village communities within the Papua New Guinea highlands. *J. Allergy Clin. Immunol.*, 75, 75–83.

FADOK, V. A., VOELKER D. R., CAMPBELL, P. A., COHEN, J. J., BRATTON, D. L. & HENSON, P. M. (1992). Exposure of phosphatidylserine on the surface of apoptotic lymphocytes triggers specific recognition and removal by macrophages. *J. Immunol.* 148, 2207–2216.

FRISCH, S. M. & FRANCIS, H. (1994). Disruption of epithelial cell-matrix intercations induces apoptosis. *J. Cell Biol.*, 124, 619–626.

FURUSE, M., ITOH, M., HIRASE, T., NAGAFUCHI, A., YONEMURA, S., TSUKITA, S. & TSUKITA. S. (1994). Direct association between occludin and ZO-1 and its possible involvement in the localization of occludin at tight junctions. *J. Cell Biol.*, 127, 1617–1626.

HALE, A. J., SMITH, C. A., SUTHERLAND. L. C., STONEMAN, V. E., LONGTHORNE, V. L. CULHANE. A. C. & WILLIAMS, G. T. (996). Apoptosis: molecular regulation of cell death. *Eur. J. Biochem.*, 236, 1–26. See also published erratum *Eur. J. Biochem.*, 237, 884.

HAWS, C., FINKBEINER, W. E. WIDDICOMBE, J. H. & WINE, JJ. (1994). CFTR in Calu-3 human airway cells: channel properties and role in cAMP-activated Cl⁻conductance. *Am. J Physiol.*, 266, L502–L512.

HERBERT C. A., ARTHUR, M. J. P., ROBINSON, C. (1996). Eosinophils augment gelatinase activity in the airway mucosa. Comparative effects as a putative mediator of epithelial injury. *Br. J. Pharmacol.*, 117, 667–674.

HERBERT, C. A., EDWARDS, D., BOOT, J. R., ROBINSON, C. (1993). Stimulated eosinophils and proteinases augment the transepithelial flux of albumin in bovine bronchial mucosa. *Br. J. Pharmacol.*, 110, 840–846.

HERBERT, C. A., KING, C. M., RING, P. C., HOLGATE, S. T., STEWART, G. A., THOMPSON, P. J., ROBINSON, C. (1995). Augmentation of permeability in the bronchial epithelium by the house dust mite allergen, Der p 1. *Am. J. Respir. Cell Mol. Biol.*, 12, 369–378.

HERBERT, C. A., OMARI, T. I., SPARROW, M. P. & ROBINSON, C. (1994). Human eosinophils and recombinant matrix metalloproteinase-2 increase the permeability of bovine and porcine airways. *Br. J. Pharmacol.*, 112, 461P.

HERBERT, C. A., HOLGATE, S. T., ROBINSON, C., THOMPSON, P. J. & STEWART, G. A. (1990). Effect of mite allergen on permeability of bronchial mucosa. Lancet 2, 1132.

HEWITT, C. R. A., BROWN, A. P., HART, B. J. & PRITCHARD, D. I. (1995). A major house dust mite allergen disrupts the immunoglobulin E network by selectivity cleaving CD23: innate protection by antiproteases. *J. Exp. Med.*, 182, 1537–1544.

HEWITT, C. R. A., HORTON, H., JONES, R. M. & PRITCHARD, D. I. (1997). Heterogeneous proteolytic specificity and activity of the house dust mite proteinase allergen Der p I. *Clin. Exp. Allergy*, 27,201–207.

HOLT, P. G. (1993). Regulation of antigen-presenting cell fiction(s) in lung and airway tissues. *Eur. Respir J.*, 6, 120–129.

HOLT, P. G. (1995). Macrophage and dendritic cell populations in the respiratory tract. In: Holgate S. T. ed. *Immunopharmacology of the respiratory system*. London: Academic Press 1–12.

HOLT, P. G., McMENAMIN, C., SCHON-HEGRAD, M. A., STRICKLAND, D., NELSON, D., WILKES, L., BILYK, N., OLIVER, J., HOLT, B. J. & McMENAMIN, P. G. (1991). Immunoregulation of asthma:control of T-lymphocyte activation in the respiratory tract. *Eur. Respir. J.*, 4, S6–S15.

MOLT, P. G., SCHON, H. M., OLIVER, J., HOLT, B. J. &, McMENAMIN, P. G. (1990). A contiguous network of dendritic antigen-presenting cells with in the respiratory epithelium. *Int. Arch. Allergy Appl. Immunol.*, 91, 155–159.

HOMBURG, C. H. E., HAAS, M., von DEM BORNE, A. E. G. Kr., VERHOEVEN, A. J., REUTELINGSPERGER, C. P. M. & ROOS, D. (995). Human neutrophils lose their surface FcγRIII and acquire annexin V binding sites during apoptosis in vitro. *Blood*, 85, 532–540.

HOWARTH, A. G., SINGER, K. L. & STEVENSON, B. R. (1994). Analysis of the distribution and phosphorylation state of ZO-1 in MDCK and nonepithelial cells. *J. Membr. Biol.*, 137, 261–270.

IBRAHIM, M. A. A., CHAIN. B. M. & KATZ, D. R. (1996). The injured cell: the role of the dendritic cell system as a sentinel receptor pathway. *Immunol. Today*, 16, 181–186.

KAYAGAKI, N., KAWASAKI, A., EBATA, T., OHMOTO, H., IKEDA, S., INOUE, S., YOSHINO, K., OKAMURA, K. & YAGITA, H. (995). Metalloproteinase mediated release of human Fas ligand. *J. Exp. Med.*, 182, 1777–1783.

KING, C., SIMPSON, R. J., MORITZ, R. L., REED, G. E., THOMPSON, P. J. & STEWART, G. A. (1996). The isolation and characterization of a novel collagenolytic serine protease allergen (Der p 9) from the dust mite, Dermatophagoides pteronyssinus. *J. Allergy Clin. Immunology*, 98, 739–747.

KOOPMAN, G., REUTELINGSPERGER, C. P. M., KUIJTEN, G. A. M., KEEHNEN, R. M. J., PALS, S. T., & van OERS, M. H. J. (1994). Annexin V for flow cytometric detection of phosphatidylserine expression on B cells undergoing apoptosis. *Blood*, 84, 1415–1420.

LOS, M., VAN DE CRAEN, M., PENNING, L. C., SCHRENK, H., WESTENDORP, M., BAEUERLE, P., DROGE, W., KRAMMER, P. H., FIERS, W. & SCHULTZ-OSTHOFF, K. (1995). Requirement of an ICE/CED-3 protease for Fas/APO-1 mediated apoptosis. *Nature*, 375, 81–83.

MAHIDA, Y. R., MAKH, S., HYDE, S. GRAY, T. & BORRIELLO, S. P. (1996). Effect of Clostridium difficile toxin A on human intestinal epithelial cells: induction of IL-8 production and apoptosis after cell detachment. *Gut*, 38, 337–347.

MARIANI, S. M., MATIBA, B., BAUMLER, C. & KRAMMER, P. H. (1995). Regulation of cell surface APO-1/Fas (CD95) ligand expression by metalloproteases. *Eur. J. Immunol.*, 25, 2303–2307.

MARTIN, S. J., O'BRIEN, G. A., NISHIOKA, W. K., McGAHON, A. J., MAHBOUBI, A., SAIDO, T, C, & GREEN, D. R. (1995). Proteolysis of Fodrin (nonerythroid spectrin) during apoptosis. *J. Biol. Chem.*, 270, 6425–6428.

MARTIN, S. J., REUTELINGSPERGER, C. P. M., McGAHON, A. J., RADER, J. A., van SCHIE R. C. A. A., LaFACE, D. M. & GREEN, D. R. (1995). Early redistribution of plasma membrane phosphatidylserine is a general feature of apoptosis regardless of the initiating stimulus: inhibition by overexpression of Bcl-2 and Abl. *J. Exp. Med.*, 182, 1545–1556.

MATZINGER, P. (1994). Tolerance, danger, and the extended family. *Annu. Rev. Immunol.*, 12, 991–1045.

OMARI, T. I. & SPARROW, M. P. (992). Epithelial disruption by proteases augments the responsiveness of porcine bronchial segments. *Clin. Exp. Pharmacol. Physiol.*, 19, 785–794.

PARRISH, E. P., STEART, P. V., GARROD, D. R. & WELLER, R. O. (1987). Antidesmosomal monoclonal antibody in the diagnosis of intracranial tumours. *J. Pathol.*, 153, 265–273.

PLATTS-MILLS, T. A. E., THOMAS, W. R., AALBERSE, R. C., BERVOLET, D., CHAPMAN, M. D., BISCHOFF, E., BRUIJNSEEL-KOOMEN, C. A. F. M., CHARPIN, D., COLLOF, M. J., EGGLESTON, P. A., EHNERT, B., GOLDSTEIN, R. A., van HAGE-HAMSTEN, M., HART, B. J., HOLGATE, S. T., HONG, C. S., JOHANSSON, S. G. O., KORGGAARD, J. & LAU, S. (1992). Dust mite allergens and asthma - report of a 2nd international workshop. *J. Allergy Clin. Immunol.*, 89, 1046–1060.

RIDGE, J. P., FUCHS E. J. & MATZINGER, P. (1996). Neonatal tolerance revisited: turning on newborn T cells with dendritic cells. *Science*, 271, 1723–1726.

ROBINSON, C. (1995). The airway epithelium: the origin and target of inflammatory airways disease and injury. In Holgate S. T., ed. *Immunopharmacology of the respiratory system*. London: Academic Press 187–207.

ROBINSON, C., KALSHEKER, N. A., SRINIVASAN, N., KING, C. M., GARROD, D. R., THOMPSON, P. J. & STEWART, G. A. (1997). On the potential significance of the enzymatic activity of mite allergens to immunogenicity. Clues to structure and function revealed by molecular characterization. *Clin. Exp. Allergy*, 27, 10–21.

SCHNEEBERGER, E. E. & LYNCH. R. D. (1 992). Structure, function and regulation of cellular tight junctions. *Am. J. Physiol.*, 262, L647–L661.

SEARS, M. R., HERBISON, G. P., HOLDAWAY, M. D., HEWITT, C. J., FLANNERY, E. M. & SILVA, P. A. (989). The relative risks of sensitivity to grass pollen, house dust mite and cat dander in the development of childhood asthma. *Clin. Exp. Allergy*, 19, 419–424.

SHAW, E. (1990). Cysteinyl proteinases and their selective inactivation. *Adv. Enzymol.*, 63, 271–347.

SHEN. B.-Q., FINKBEINER, W. E., WINE, J. J., MRSNY, R. J. & WIDDOCOMBE, J. H. (1994). Calu-3: a human airway epithelial cell line that shows cAMP-dependent Cl⁻secretion. *Am. J. Physiol.*, 266, L493–L501.

SMITH, P. K., KROHN, R. I., HERMANSON, G. T., MALLIA, A. K., GARTNER, F. H., PROVENZANO, M. D., FUJIMOTO, E. K., GOEKE, N. M., OLSON, B. J. & KLENK, D. C. (1985). Measurement of protein using bicinchoninic acid. *Anal. Biochem.*, 150, 76–85 (and published erratum, 163, 279 (1987)).

STEVENSON, B. R., SICILIANO, J. D., MOOSEKER, M. S., GOODENOUGH, D. A. (1986). Identification of ZO-1: a high molecular weight polypeptide associated with the tight junction (zonulae occludens) in a variety of epithelia. *J. Cell Biol.*, 103, 755–766.

STEWART, G. A. (1994). Molecular biology of allergens. In: Busse WW, Holgate ST, eds: *Asthma and rhinitis*. Oxford: Blackwell Science, 898–932.

STEWART, G. A., WARD, L. D., SIMPSON, R. J. & THOMPSON, P. J. (1992). The group III allergen from the house dust mite Dermatophagoides pteronyssinus is a trypsin-like enzyme. *Immunology* 75, 29–35.

STUART, R. O., DUN, A., PANICHAS, M., HEBERT, S. C., BRENNER, B. M. & NIGAM, S. K. (1994). Critical role for intracellular calcium in tight junction biogenesis. *J. Cellul. Physiol.* 159, 423–433.

STUART, R. O. & NIGAM, S. K. (1995). Regulated assembly of tight junctions by protein kinase C. *Proc. Natl. Acad. Sci. USA*, 92, 6072–6076.

TANAKA, M., SUDA, T., HAZE, K., NAKAMURA, M., SATO, K., KIMURA, F., MOTOYOSHI, K., MIZUKI. M., TAGAWA, S., OHGA, S., HATAKE, K., DRUMMOND, A. H. & NAGATA, S. (996). Fas ligand in human se rum. *Nature Med.*, 2, 317–322.

TOPHAM, C. M., SRINIVASAN, N., THORPE, C. J., OVERINGTON, J. P. & KALSHEKER, N. A. (1994). Comparative modelling of major house dust mite allergen Der p I: structure validation using an extended environmental amino acid propensity table. *Protein Engng.*, 7, 869–894.

TOVEY, E. R., CHAPMAN, M. D. & PLATTS-MILLS, T. A. E. (1981). Mite faeces are a major source of house dust allergens. *Nature*, 289, 592–593.

VERMES, I., HAANEN, C., STEFFENS-NAKKEN, H. & REUTELINGSPERGER, C. (1994). A novel assay for apoptosis flow cytometric detection of phosphatidylserine expression on early apoptotic cells using fluorescein labelled Annexin V. *J. Immunol. Methods*, 184, 39–51.

VOLK, T., VOLBERG, T., SABANAY, I. & GEIGER, B. (1990). Cleavage of A-CAM by endogenous proteinases in cultured lens cells and in developing chick embryos. *Dev. Biol.*, 139,314–326.

YASUEDA, H., MITA, H. & AKIYAMA, K., SHIDA, T., ANDO, T., SUGIYAMA, S. & YAMAKAWA, H. (1993). Allergens from Dermatophagoides mites with chymotryptic activity. *Clin. Exp. Allergy*, 23, 384–390.

ZHONG, Y., ENOMOTO, K., ISOMURA, H., SAWADA, N., MINASE, T., OYAMADA, M., KONISHI, Y. & MORI, M. (1994). Localization of the 7H6 antigen and tight junctions correlates with the paracellular barrier function of MDCK cells. *Exp. Cell. Res.*, 214, 614–620.

LEGENDS TO FIGURES

FIG. 1.

SDS-PAGE (panel a) and immunoblot analysis (panel b) of HDM proteinase fractions. Key to lanes in panel a: immunoaffinity purified Der p 1 (1); HDM cysteine proteinase fraction (2) and HDM serine proteinase fraction (3). Proteins were visualized by coomassie blue staining. Panel b shows the immunoblot prepared from the gel in panel a. Proteins were detected using mAb 5H8 (anti-Der p 1) and visualized by ECL technique. Note the detection of immunoreactive proteins by mAb 5H8 in the serine proteinase fraction in addition to the expected immunoreactivity of the cysteine proteinase fraction. Filled circles indicate mass calibration standards and arrows indicate apparent molecular masses of bands calculated from the mobilities of dye labelled standards.

FIG. 2.

Dilution-response curves showing the effects of 18 h exposure of cell monolayers to the serine proteinase fraction prepared from HDM cultures. Panel (a) shows the mannitol permeability of MDCK epithelial cells under control conditions (serum-free EMEM alone) and following treatment (proteinase fraction diluted in serum-free EMEM). Panel (b) depicts similar studies performed in Calu-3 bronchial epithelial cells. Data are mean ± s.e. mean in 4–6 experiments. Proteinase allergen activity (expressed in azocoll units $ml^{-1}$) is indicated by the numbers under the filled bars. Asterisks indicate statistically significant differences with respect to the untreated control response (serum-free EMEM medium) for each cell type .

FIG. 3.

Inhibition of the effects of HDM proteinase fractions on mannitol permeability in MDCK cell monolayers. Panel (a) shows the effects of E-64 ($10\mu M$) on the effect produced by the cysteine proteinase fraction (80 azocoll units $ml^{-1}$). Control cells were exposed to serum-free EMEM containing 0.5 mM reduced glutathione. Panel (b) depicts the effcts of AEBSF ($100\mu M$) on the effects of the serine proteinase fraction (127 azocoll units $ml^{-1}$). Data are mean i s.e. mean in 3–5 experiments. Contact time was 18 h in all cases. In both panels (a) and (b) statistically significant differences exist between the permeabilities of control and proteinase treated monolayers and also between the monolayers treated with the proteinases in the presence and absence of inhibitors. Significant comparisons are shown in the Figure by the bracketing lines and indicated probability values.

FIG. 4.

Panel (a) illustrates the effects of $100\mu M$ AEBSF on the changes in mannitol permeability evoked in Calu-3 cell monolayers following 18 h exposure to the cysteine proteinase fraction (80 azocoll units $ml^{-1}$). Data are mean ± s.e. mean in 3 experiments. Panel (b) illustrates the effects of $10\mu M$ E-64 on the changes in mannitol permeability evoked in Calu-3 cell monolayers following 18 h exposure to the serine proteinase fraction (94 azocoll units $ml^{-1}$). Data are mean ± s.e. mean in 3 experiments. In both examples, the control cells were treated with serum-free EMEM medium alone (with 0.5 mM reduced glutathione in the case of the cysteine proteinase fraction).

FIG. 5. Immunostaining of the TJ protein ZO-1 (panels a-e) and the desmosomal plaque protein desmoplakin (panels f–j) in MDCK cell monolayers. Panels a,f show immunostaining of cells exposed to serum-free EMEM as control. The pattern of immunostaining after treatment with the cysteine proteinase fraction (80 azocoll units $ml^{-1}$) is shown in panels b,g and the modification of this response by E-64 ($10\mu M$) in panels c,h. The pattern of immunostaining after treatment with the serine proteinase fraction (94 azocoll units $ml^{-1}$) is shown in panels d,i and the modification of this response by AEBSF ($100\mu M$) in panels e,j.

FIG. 6.

Measurement of LDH release following treatment of MDCK or Calu-3 cells with HDM proteinase fractions for 18h. Panel a shows the lack of release of LDH from cells under control conditions until the monolayer was subjected to hypotonic lysis. Panel a also shows that treatment with the cysteine proteinase fraction (80 azocoll units $ml^{-1}$ after activation with 0.5 mM reduced glutathione) resulted in no release of LDH into the medium during the treatment period. Note that all of the cells were detached from the wells during treatment and that hypotonic lysis of the detached cells resulted in recovery of the same amount of LDH activity measured in the control cells. Panel b illustrates a similar experiment using the serine proteinase fraction (114 azocoll units ml$^{-1}$). Note that not all of the cells were detached during the treatment period, but that the sum of LDH activity in lysed adherent and lysed detached cells correspond to the amount detected in control cells. Panels c and d show similar experiments performed in Calu-3 cells. Note that there was a small background release of LDH from these cells (<10% total cellular LDH) under control conditions and that this was not significantly altered by proteinase treatment. Data shown are mean + s.e. mean in 4 experiments.

FIG. 7.

Agarose gel electrophoresis of DNA (panels a,b) and cellular staining with AV and PI (panels c–j) following treatment of MDCK and Calu-3 cells with HDM proteinase fractions. Panel a shows proteinase-induced DNA fragmentation in MDCK cells. Key to lanes: DNA markers (1,10); untreated cells (2,3); cells treated for 18 h with 10μM camptothecin (positive control) (4,5); cells treated for 18 h with serine proteinase fraction (114 azocoll units ml$^{-1}$) (6,7) and cells treated with cysteine proteinase fraction (80 azocoll units ml$^{-1}$ after activation) for 18 h (8,9). Panel b shows DNA fragmentation in Calu-3 cells. Key to lanes: DNA markers (1,11); untreated cells (2); cells treated for Xh with serine proteinase fraction (94 azocoll units ml$^{-1}$) (3); cells treated with cysteine proteinase fraction (80 azocoll units ml$^{-1}$ after activation) for 18 h (4); untreated cells in the presence of BB-250 (5μM) (5); as lane 3, but cells treated in the presence of 5μM BB-250 (6); as lane 4, but cells treated in the presence of 5μM BB-250 (7); untreated cells in the presence of 10μM E-64 (8); as lane 3, but cells treated in the presence of 10μM E-64 (9); as lane 4, but cells treated in the presence of 10μM E-64 (10). Panels c-f show fluorescence microscopy of AV and PI (e,f) staining of Calu-3 cell monolayers under control conditions (c,e) and following treatment for 18 h with the serine proteinase fraction (135 azocoll units ml$^{-1}$) (d,f). Panels c,d show the staining pattern under blue light excitation and e,f show that under green light excitation. Panels g–j show examples from MDCK cell monolayers with the same layout as panels c–f. In both cell types, note the virtual absence of AV and PI staining in untreated cells. In panels d,f the staining pattern partially circumscibes an area of cell detachment in the monolayer and note that some cells exhibit both AV and PI staining. In panels h,j the majority of stained cells are positive for both AV and PI and no significant detachment of cells from the substratum was evident.

What is claimed is:

1. A method of treating a subject for the prevention or treatment of an allergic condition in which an allergen traverses an epithelial barrier comprising administering Lo the subject e therapeutically effective amount of an inhibitor of cysteine proteinase activity in conjunction with an inhibitor of serine proteinase activity.

2. The method according to claim 1 wherein the allergeic condition is asthma.

3. The method according to claim 1 wherein the allergic condition is an allergic condition selected from rhinitis, allergic conjunctivitis, atopic dermatitis or food allergies.

4. The method according to claim 1 wherein the inhibitor of serine proteinase activity is not trypsin.

5. The method according to claim 1 wherein the inhibitor of serine proteinase activity is an allergen serine proteinase inhibitor.

6. The method according to claim 5 wherein the allergen serine proteinase inhibitor inhibits Der p3, Der p6 or Der p9.

7. The method according to claim 1 wherein said method comprises administering E-64 (L-trans-epoxysuccinyl-leucylamido-(4-guanidines) butane) in conjunction with AEBSF (4-(2-amino ethyl)-benzenesulphonyl fluoride hydrochloride).

* * * * *